(12) United States Patent
Xiao

(10) Patent No.: US 7,787,949 B2
(45) Date of Patent: Aug. 31, 2010

(54) BIOLOGICAL PACEMAKER COMPOSITIONS AND SYSTEMS INCORPORATING INTERSTITIAL CELLS OF CAJAL

(75) Inventor: Yong-Fu Xiao, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 672 days.

(21) Appl. No.: 11/554,431

(22) Filed: Oct. 30, 2006

(65) Prior Publication Data

US 2008/0103536 A1 May 1, 2008

(51) Int. Cl.
*A61N 1/02* (2006.01)
(52) U.S. Cl. .......................................... 607/9
(58) Field of Classification Search .................. None
See application file for complete search history.

(56) References Cited

U.S. PATENT DOCUMENTS

| | | | | |
|---|---|---|---|---|
| 5,103,821 | A | * | 4/1992 | King ............................... 607/9 |
| 6,214,620 | B1 | | 4/2001 | Johns et al. |
| 6,690,970 | B1 | | 2/2004 | Taheri et al. |
| 6,849,611 | B2 | | 2/2005 | Rosen et al. |
| 2002/0001577 | A1 | | 1/2002 | Haverich et al. |
| 2003/0104568 | A1 | * | 6/2003 | Lee ........................... 435/69.1 |
| 2004/0215251 | A1 | * | 10/2004 | Sharma et al. .................. 607/9 |
| 2004/0254134 | A1 | | 12/2004 | Marban et al. |
| 2005/0021089 | A1 | | 1/2005 | Sharma |
| 2007/0098754 | A1 | | 5/2007 | Tropsha et al. |
| 2008/0103537 | A1 | | 5/2008 | Sigg et al. |

FOREIGN PATENT DOCUMENTS

| | | |
|---|---|---|
| EP | 0525958 A | 2/1993 |
| WO | WO 02/087419 | 11/2002 |
| WO | WO 02/098286 | 12/2002 |
| WO | WO 2004/096290 | 11/2004 |
| WO | WO 2005/009477 | 2/2005 |
| WO | WO 2005/062890 | 7/2005 |
| WO | WO 2005/062958 | 7/2005 |
| WO | WO 2006/044589 | 4/2006 |
| WO | WO 2008/073577 | 6/2008 |

OTHER PUBLICATIONS

Dudek, Ronald W. "High-Yield Physiology" Lippincott Williams & Wilkins, 2007 ISBN 078174587X, 9780781745871 p. 123.*

(Continued)

*Primary Examiner*—George R Evanisko
*Assistant Examiner*—Andrew Hayes
(74) *Attorney, Agent, or Firm*—Stephen W. Bauer

(57) ABSTRACT

A biological pacemaker composition for implantation into cardiac tissue includes an effective amount of interstitial cells of Cajal (ICC) to produce or conduct pacing stimuli and thereby modulate cardiac contraction. The biological pacemaker may be included as part of a heart pacing system that includes an implantable electric pacemaker for producing backup pacing stimuli if the at least one biological pacemaker is unable to modulate cardiac contraction at a predetermined pacing rate. Methods for preventing cardiac pacing or conduction dysfunction in a heart include implanting the biological pacemaker or the heart pacing system into the heart.

9 Claims, 5 Drawing Sheets

OTHER PUBLICATIONS

Sangren K et al. "Survival of neurons and interstitial cells of Cajal after autotransplantation of myentric ganglia from small intestin in lethat spotted mouse."; Pediatric Surgery International 2000; vol. 16, No. 4, 2000; pp. 272-276; XP002477979.*

Hinescu, et al. Interstitial Cajal-like cells (ICLC) in human myocardium J. Cell Mol. Med, vol. 9, No. 4, Nov. 2005, pp. 972-975.*

Huizinga et al., "About the presence of interstitial cells of Cajal outside the musculature of the gastrointestinal tract", *Journal of Cellular and Molecular Medicine*, vol. 9, No. 2, 2005, pp. 468-473.

Chen et all, "Selective Labeling and Isolation of Functional Classes of Interstitial Cells of Cajal of the Human and Murine Small Intestine", *American Journal Physiol Cell Physiol*, Aug. 30, 2006, pp. 1-42.

Sandgren K. et al., "Survival of Neurons and Interstitial Cells of Cajal after Autotransplantation of Myenteric Ganglia from Small Intestine in the Lethal Spotted Mouse."; Pediatric Surgery International 2000; vol. 16, No. 4, 2000; pp. 272-276; XP002477979.

J.D. Huizinga et al.; "Interstitial Cells of Cajal as Targets for Pharmacological Intervention in Gastrointestinal Motor Disorders"; Trends in Pharmacological Sciences, Elsevier, Haywarth, GB; vol. 18, No. 10, Oct. 1997; pp. 393-403; XP004099896.

M. Takaki; "Gut pacemaker cells: The Interstitial Cells of Cajal (ICC)"; Journal of Smooth Muscles Research; vol. 39, No. 5, Oct. 2003; pp. 137-161; XP002477948.

Jonathan C.F. Lee et al., "Generation of slow waves in membrane potential is an intrinsic property of interstitial cells of Cajal", *American J Physiol Gastrointest Liver Physiol*, vol. 277, pp. G409-G423, 1999.

Thomsen et al., "Interstitial Cells of Cajal Generate a Rhythmic Pacemaker Current" Nature Medicine, vol. 4, No. 7, Jul. 1998, pp. 848-851.

Takaki, "Gut Pacemaker Cells: the Interstitial Cells of Cajal (ICC)"; J Smooth Muscle Res. Oct. 2003; 39(5), pp. 137-161.

Yanagida et al., "Intestinal Surgical Resection Disrupts Electrical Rhythmicity, Neural Responses, and Interstitial Cell Networks", Gastroenterology vol. 127, No. 6, 2004, pp. 1748-1759.

Huizinga et al., "About the Presence of Interstitial Cells of Cajal Outside the Musculature of the Gastrointestinal Tract" J. Cell. Mol. Med., vol. 9, No. 2, Jun. 2005, pp. 468-473.

Hinescu et al., "Interstitial Cajal-like cells (ICLC) in Human Atrial Myocardium" J. Cell. Mol. Med, vol. 9, No. 4, Nov. 2005, pp. 972-975.

Popescu et al., "Insights into the Interstitium of Ventricular Myocardium: Interstitial Cajal-like cells (ICLC)", J. Cell. Mol. Med., vol. 10, No. 2, May 2006, pp. 429-458.

McKay et al., "Muscarinic Regulation of ERG K+ Currents in Interstitial Cells of Cajal"; J Pharmacol Exp Ther. Aug. 31, 2006.

Sanders, "Interstitial Cells of Cajal at the Clinical and Scientific Interface"; J Physiol., Aug. 31, 2006.

Chen et al., "Selective Labeling and Isolation of Functional Classes of Interstitial Cells of Cajal of the Human and Murine Small Intestine" The American Journal of Physiology—Cell Physiology, Aug. 2006, pp. 1-42.

Ye et al., "IL-9 Enhances Growth of ICC, maintains Network Structure and Strengthens Rhythmicity of Contraction in Culture" J. Cell. Mol. Med., Vo. 10, No. 3, Aug. 2006, pp. 687-694.

* cited by examiner

BIOLOGICAL PACEMAKER COMPOSITIONS AND SYSTEMS INCORPORATING INTERSTITIAL CELLS OF CAJAL

FIELD OF THE INVENTION

The present invention relates to systems, compositions, and methods for providing curative therapy for cardiac dysfunction, and particularly relates to compositions and methods that include or introduce biological curative therapeutic agents for treating arrhythmias and cardiac pacing dysfunction.

BACKGROUND OF THE INVENTION

Cardiac contraction in a healthy human heart is initiated by spontaneous excitation of the sinoatrial ("SA") node, which is located in the right atrium. The electrical impulse generated by the SA node travels to the atrioventricular ("AV") node where it is transmitted to the bundle of His and to the Purkinje network. The fibers in the Purkinje network branch out in many directions to facilitate coordinated contraction of the left and right ventricles thus providing natural pacing. In some disease states, the heart loses some of its capacity to pace properly. Such dysfunction is commonly treated by implanting a pacemaker.

While effectively improving the lives of many patients, implantable pacemakers rely on a self-contained power source such as a battery and consequently have a limited lifetime before the power source is in need of replacement. Hence, an otherwise healthy patient may require multiple surgeries to replace the power source or the entire implantable pacemaker. In addition, implantable pacemaker batteries are large and are usually the bulkiest pacemaker component. A pacemaker's size and capability for implantation in different body regions are typically dictated by the battery size. Also, implantable pacemakers have very limited or no capacity for directly responding to the body's endogenous signaling the way the SA node responds to such signaling, i.e. by a modulation of the heart rate relative to the physiological and emotional state (e.g. sleep, rest, stress, exercise).

Recently, biological methods of influencing a patient's cardiac cells have been developed, some of which include administering biopharmaceutical compositions that affect cardiac pacing. Developments in genetic engineering have produced methods for genetically modifying cardiac cells to convert non-pacemaking cardiac cells to cardiac cells. For example, U.S. Pat. No. 6,214,620 describes a method for modulating the excitability of ventricular cells by controlling the regulation of the expression of certain ion channels (e.g. $K^+$ channels). PCT Publication No. WO 02/087419 and WO 05/062890A3 describe methods and systems for modulating electrical behavior of cardiac cells by genetic modification of inwardly rectifying $K^+$ channels ($I_{K1}$) in quiescent ventricular cells. PCT Publication No. WO 02/098286 and WO 05/062958A2 describe methods for regulating pacemaker function of cardiac cells with HCN molecules (HCN 1, 2, 3 or 4 isoforms of the pacemaker current $I_f$). It is thought that these and other biological methods and systems may be used as stand-alone cardiac therapies. However, to ensure continuing proper cardiac function, U.S. Publication No. US 2004/0215251 discloses the use of an implantable electrical pacemaker as a backup pacing device, with a biological pacemaker expressing features that regulate the primary pacing functions.

While it is clear from the previously-discussed recent developments that genetic modifications to cardiac cells provide numerous benefits in treating heart arrhythmia, there is also a need for biological pacemakers that function endogenously without requiring genetic modifications. Furthermore, there is a need for the use of autologous biological pacemaker sources to improve the probability for their successful implantation and incorporation in a patient's cardiac tissue with a minimal likelihood for immunorejection to occur.

BRIEF SUMMARY OF THE INVENTION

A biological pacemaker composition is provided for implantation into cardiac tissue. The composition includes an effective amount of interstitial cells of Cajal (ICC) to produce or conduct pacing stimuli and thereby modulate cardiac contraction.

A heart pacing system is also provided. The system includes at least one biological pacemaker including ICC for producing or conducting primary pacing stimuli that modulate cardiac contraction. The system further includes an implantable electric pacemaker for producing backup pacing stimuli that modulate cardiac contraction if the at least one biological pacemaker is unable to modulate cardiac contraction at a predetermined pacing rate.

Methods are also provided for preventing cardiac pacing or conduction dysfunction in a heart. According to one embodiment, a method includes implanting into the heart an effective amount of ICC to produce or conduct pacing stimuli and thereby modulate cardiac contraction. According to another embodiment, a method includes implanting into the heart at least one biological pacemaker including ICC for producing or conducting primary pacing stimuli that modulate cardiac contraction, and also implanting an implantable electric pacemaker for producing backup pacing stimuli that modulate cardiac contraction if the at least one biological pacemaker is unable to modulate cardiac contraction at a predetermined pacing rate.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
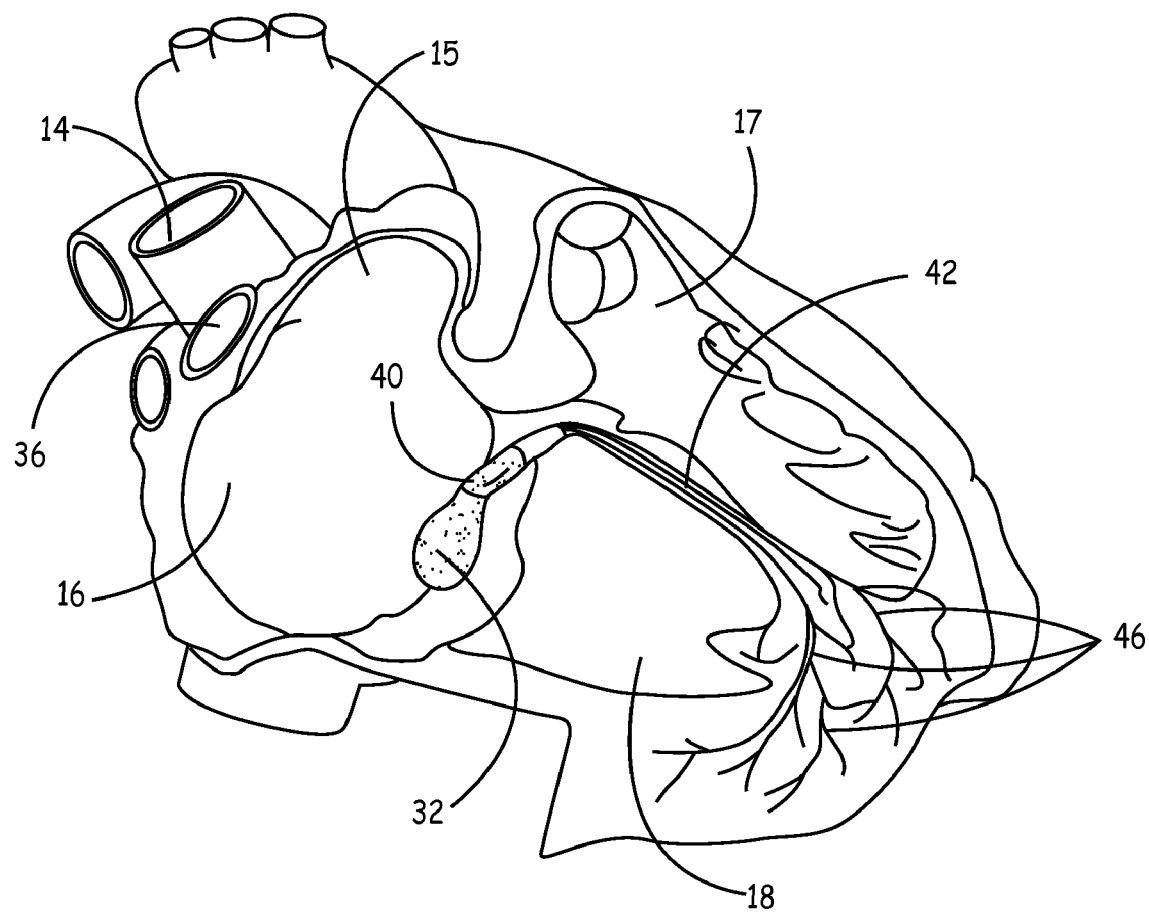
FIG. 1 is side view of the right side of a heart having an anterior-lateral wall peeled back to present a portion of a heart's intrinsic conduction system and chambers of a right atrium and a right ventricle.

FIG. 1 is side view of the right side of a heart having an anterior-lateral wall peeled back to present a portion of a heart's intrinsic conduction system and chambers of a right atrium 16 and a right ventricle 18. Pertinent elements of the heart's intrinsic conduction system include the SA node 36, the AV node 32, the bundle of His 40, the right bundle branch 42, and the Purkinje fibers 46. The SA node 36 is shown at a junction between a superior vena cava 14 and the right atrium 16. An electrical impulse initiated at the SA node 30 travels rapidly through the right atrium 16 and the non-illustrated left atrium to the AV node 32. At the AV node 32, the impulse slows to create a delay before passing on through the bundle of His 40, which branches, in an interventricular septum 17, into the right bundle branch 42 and the non-illustrated left bundle branch and then, apically, into the Purkinje fibers 46. The impulse then travels rapidly throughout the right ventricle 18 and the non-illustrated left ventricle. This electrical impulse flow creates an orderly sequence of atrial and ventricular contraction to efficiently pump blood through the heart. If a portion of the heart's intrinsic conduction system becomes dysfunctional, efficient pumping is compromised.

Therapeutic methods of the present invention include implantation of an effective amount of interstitial cells of Cajal (ICC) to the cardiac cells to produce a biological pacemaker that improves cardiac action potential conduction or modulate conduction by increasing or decreasing the intrinsic pacing rate of such cells. The ICC are myoid cells that form networks that are widely distributed within the submucosal, intramuscular, and inter-muscular layers of the gastrointestinal tract from the esophagus to the internal anal sphincter. Spontaneous active pacemaker currents that may be recorded as plateau and slow potentials are generated in the gut by the ICC. These pacemaker currents drive the spontaneous electrical and mechanical activities of the gut smooth muscle cells by mediating or transducing inputs from enteric motor nerves to the smooth muscle syncytium. Different populations of ICC exist in the gut muscle coat, and each population has different region-specific location and region-specific ultrastructural features. However, all ICC subpopulations share some ultrastructural and functional characteristics as reported in Huizinga et al., *J. of Cellular and Molecular Medicine,* 9:468 (2005). At the microscopy level, the ICC are recognizable as a network of cells that express the c-kit receptor. However, there are other c-kit positive cells that are not ICC, and intrastructural features are consequently also used to identify ICC. Generally speaking, ICC are identifiable among all other cell types in an interstitial position between nerve fibers and smooth muscle cells by features that include bundles of mainly intermediate filaments distributed throughout the interstitium, several microtubules, an extended smooth endoplasmic reticulum, few ribosomes, and a variable number of cisternae of rough endoplasmic reticulum, a large Golgi apparatus, many mitochondria and caveolae, and the presence of a basal lamina. Furthermore, the ICC have a unique functional relationship with both smooth muscle cells and intrinsic nerves.

Although the ICC are prevalent in the gastrointestinal tract, interstitial cells have been identified in recent years in the vasculature, urinary tract, glands, and other organs. The morphologies and functions for these interstitial cells are just beginning to be clarified, although it is likely that subtypes will be classified as ICC even though they are found outside of the gut. Hence, the terms "ICC" and "ICC-rich tissue" refer herein to both the conventional interstitial cells as previously described, and also to non-gut interstitial tissues for implantation into cardiac tissue for performing pacemaking functions and therapies for conduction damage or block. A discussion of criteria that may be used to identify ICC outside of the gut is reported in the previously-cited article by Huizinga et al. (2005).

Figure 2:
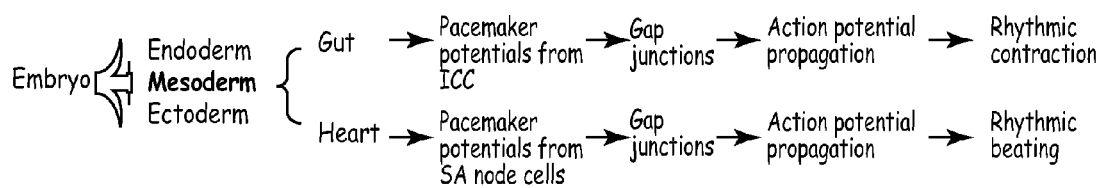
FIG. 2 is a flow chart depicting a comparison of the generation of spontaneous movement in the gut and in the heart, beginning at the embryological stage.

The embryological origin of ICC is the mesoderm, which is the same embryonic germ layer from which heart cells originate. FIG. 2 is a flow diagram depicting a comparison of the generation of spontaneous movement in the gut and in the heart, beginning at the embryological stage. As depicted, the pacemaker current-generating ICC from the gut originate from the embryonic mesoderm, which is also the germ layer from which the pacemaker current-generating SA node cells originate. In order for rhythmic contraction to occur, gap junctions are formed in both the gut and cardiac tissue. Gap junctions occur in both tissues due in part to both the ICC and the SA node cells forming conductive networks by expressing connexin isoforms including gap junction protein connexin 43 (Cx43), which is essential for proper operation of the heart conduction pathway. Furthermore, each of the ICC and the SA node cells express ion channels that function in identical or similar manners to propagate action potentials. In the gut, the action potentials initiate rhythmic contractions, while in the heart the action potentials initiate a steady heart rhythm.

Figure 3:
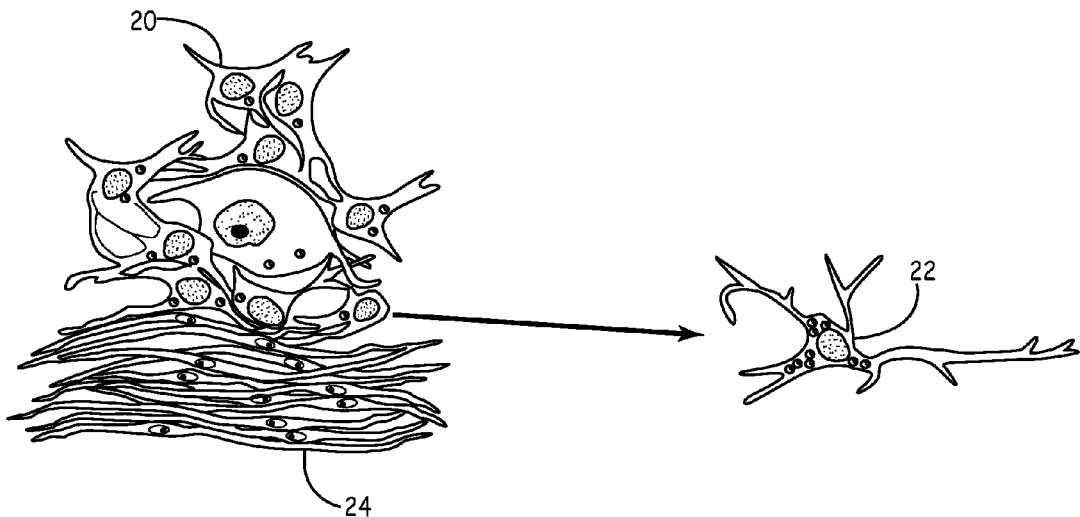
FIG. 3 is a flow chart depicting development of interstitial cells of Cajal from embryonic cells in the myenteric region into their mature phenotypes.

FIG. 3 is a flow diagram depicting ICC development from embryonic cells in the myenteric region into their mature phenotypes. ICC develop from mesenchymal precursors 20 that express c-kit and are found adjacent to circular smooth muscle cells 24. Such precursors 20 that are not stimulated by the Kit pathway mature into longitudinal smooth muscle cells. Those precursors 20 that receive stimulation by the Kit pathway mature into ICC 22. Since the ICC have origins and development similar to heart cells, spontaneous rhythm in both ICC and cardiac pacemaker cells involves many similar mechanisms along with the use of similar ion channels. As previously discussed, the similarities between the ICC and SA node cells makes the ICC cells, or ICC-rich tissues, viable specimens for implantation into diseased or unhealthy cardiac tissue to form a biological pacemaker. As the body has rich resources of ICC, implantation and biological pacemaker formation can be performed using autologous ICC, reducing risks and additional treatments for immunorejection. The biological pacemaker of the present invention is therefore capable of benefiting virtually any patient in need.

Figure 4:
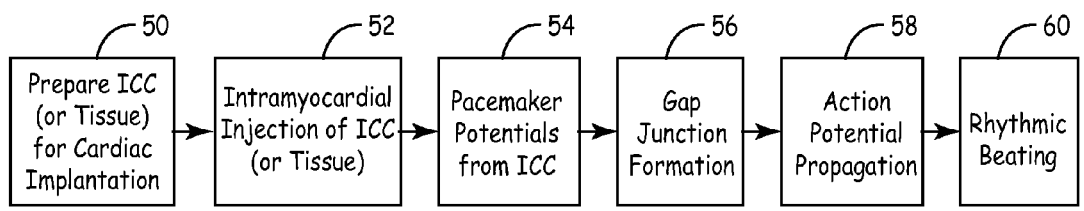
FIG. 4 is a flow chart depicting a method for treating an arrhythmia-producing heart blockage or disease according to an embodiment of the present invention.

Turning now to FIG. 4, a flow diagram depicts a method for treating an arrhythmia-producing heart disease or conduction blockage according to an embodiment of the present invention. As step 50, ICC or ICC-rich tissue is prepared for cardiac implantation. Tissue and cell extraction and isolation methods are performed using well established methods. For example, if cells are to be implanted instead of ICC-rich tissue, the cells may be cultured using conventional isolation and culturing methods such as those described in Lee et al., *Am J. Physiol Gastrointes Liver Physiol,* 277:G409 (1999), and in Redelman et al., *Am. J. Physiol. Cell Biol.,* [Epub ahead of print] (2006) and any preferential modifications thereto. Next, the ICC or ICC-rich tissue is implanted into a targeted heart region as step 52. According to one exemplary method, a patient whose SA node 36 has experienced a dysfunction such as a blockage or disease will undergo implantation or transimplantation of ICC or ICC-rich tissue into an atrial appendage 15. Pacemaker potentials are produced from the implanted ICC as step 54, although it may take some time for conductive networks to be formed between the ICC and the SA node cells or other adjacent cardiac tissue. As step 56, gap junctions and conductive networks are formed in the cardiac tissue by the newly implanted ICC due in part to ICC and the SA node cells expressing gap junction protein Cx43, which as previously discussed is essential for proper operation of the heart conduction pathway. Furthermore, each of the ICC and the SA node cells express ion channels that function in identical or similar manners to propagate action potentials as step 58. The action potentials produced by the biological pacemaker produce rhythmic heart contractions as step 60.

ICC has sufficiently fast endogenous pacing to provide numerous therapies to a heart that is diseased. For example, if the ICC are implanted into the SA node 36, the cells form a biological pacemaker that stimulates the right atrium 16 downstream of the dysfunctional SA node 36, and the stimulating pulse travels on to the AV node 32, the bundle of His 40, and the Purkinje fibers 46 to restore physiological contraction of the heart. As cardiac disease or dysfunction may originate in a variety of heart regions apart from the SA node 36, other exemplary methods of the present invention include implanting ICC or ICC-rich tissue in or downstream of any dysfunctional heart region along the conduction pathway to form a biological pacemaker and thereby overcome effects created by the blockage or disease. The steady rhythm produced or mediated by the ICC makes the cells, or ICC-rich tissue, suitable for cardiac implantation to treat or cure mild to serious bradycardia. Furthermore, because ICC express gap junction protein Cx43 and form conductive networks with adjacent cells, intramyocardial transplantation of ICC or ICC-rich tissue is an effective therapy for repairing atrial-ventricular conduction block or damage to various heart regions including the AV node, the SA node, the atria, and the ventricles, to name a few examples. Similarly, another exemplary therapy according to the present invention includes implanting ICC or ICC-rich tissue into an infarct scar or in myocardium with cardiomyopathy to improve action potential conduction and cardiac formation. The ICC also produce a sufficiently steady rhythm to provide therapies for both fast and slow arrhythmia. For example, according to an exemplary embodiment ICC or ICC-rich tissue is implanted into the AV node region to attenuate ventricular tachycardia caused by overdriving of atrial flutter or atrial fibrillation. According to another exemplary embodiment, ICC are co-transplanted with other cell types for myocardial repair. For example, transplantation of skeletal myoblastic cells improves diseased heart function, but may cause cardiac arrhythmias because the endogenous myoblasts can not form gap junctions among the implanted myoblasts and also among host cardiomyocytes and implanted myoblasts. The inability for proper gap junction formation may slow action potential conduction or cause conduction block. Since the ICC form conduction networks, co-transplantation of ICC with other suitable cell types including myoblasts, hematopoietic stem cells, and bone marrow stem cells enhances the formation of conduction networks in cell-implanted myocardium and reduces the chance of arrhythmias.

Figure 5:
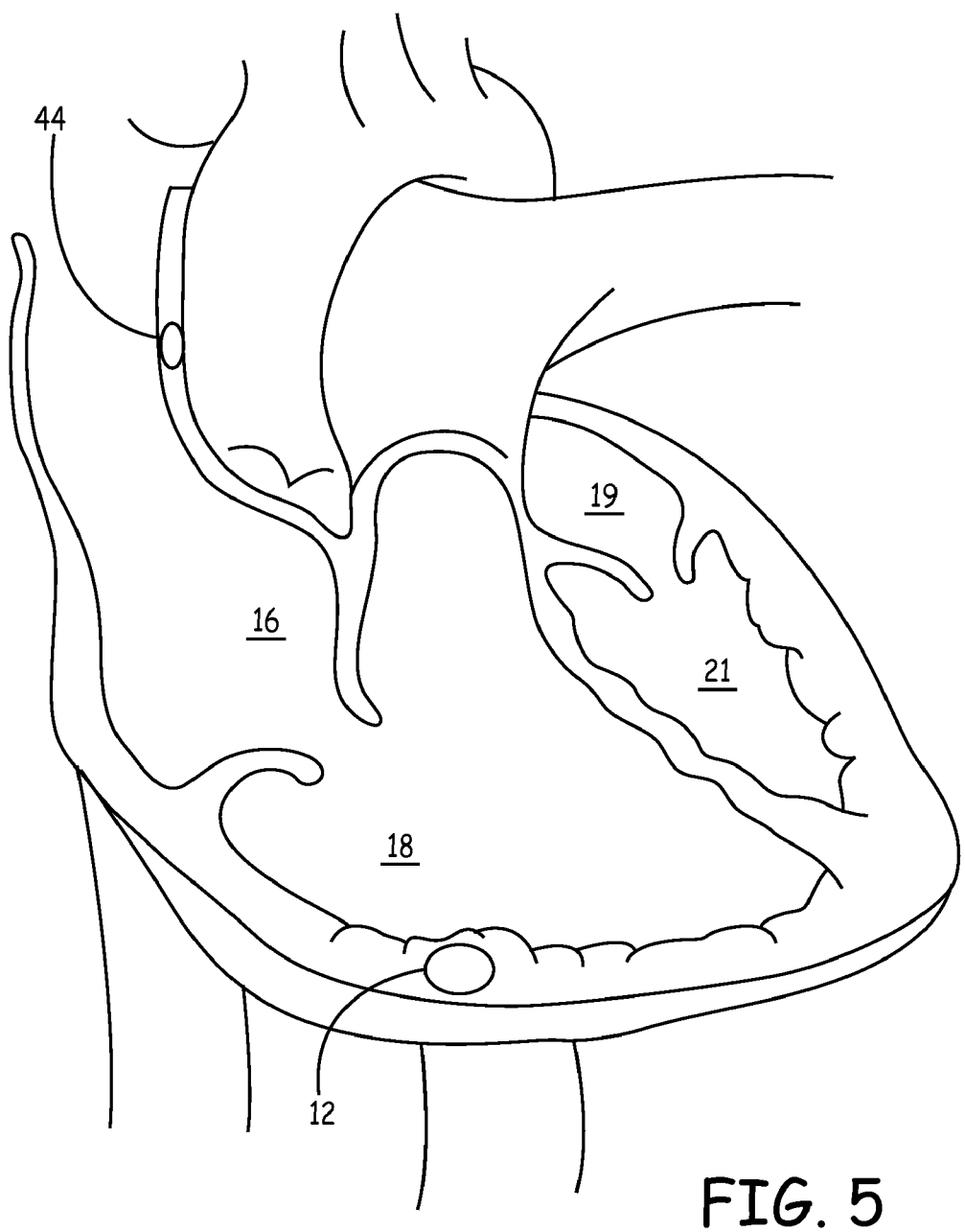
FIG. 5 is a cross-sectional view of a heart having a plurality of biological pacemakers implanted in the right ventricle and the right atrium according to an embodiment of the invention.

To illustrate how ICC or ICC-rich tissue can be used to form biological pacemakers in various heart regions, or as a therapy for conduction block or damage, FIG. 5 depicts a heart, illustrated as a cross-sectional view to reveal the right atrium 16, the left atrium 19, the right ventricle 18, and the left ventricle 21. A ventricular biological pacemaker 12 is implanted in a wall of the right ventricle 18. Also, an atrial biological pacemaker 44 is implanted in a wall of the right atrium 16, although having a plurality of biological pacemakers in different heart regions is not a necessary element of the invention. Although the biological pacemakers 12 and 44 are depicted as singular masses, it will be appreciated from the preceding and following discussion that each biological pacemaker is a network of ICC that may be distributed about a widespread heart region, or a plurality of heart regions. Furthermore, as used herein the term "biological pacemaker" represents one or more networks of ICC that are incorporated into cardiac tissue even though the ICC networks may be used for conduction block or damage therapies instead of or in addition to heart pacing functions. Also, the terms "implanted" and "implantation" refer to any suitable method for incorporating the ICC into the cardiac tissue, such as transplantation methods and injection methods.

The ventricular biological pacemakers 12 and 44, or any other backup biological pacemakers that may be used in accordance with the present invention, may be naturally suppressed in their expression when the heart is beating above a predetermined threshold pace. For example, the ICC forming the atrial biological pacemaker 44 may endogenously cause the right atrium 16 to conduct at a physiological rate of between 30 and 60 beats per minute at rest. When the heart is experiencing normal or near-normal SA nodal conduction, the right ventricle will conduct at a physiological rate of 60 to 100 beats per minute at rest, and expression of the biological pacemaker 44 will be suppressed in the same manner that the heart's natural escape rhythm is naturally suppressed during normal heart rhythm. However, if SA nodal conduction is insufficient for the right atrium to depolarize, the heart's natural escape rhythm is endogenously produced and causes the right ventricle 18 to autonomously depolarize at a pace of approximately 30 beats per minute. According to the present invention, the biological pacemaker 44 will be expressed in such conditions, causing the right atrium 16 to depolarize at a higher rate than at the endogenous escape rhythm, the faster biological pacemaker-induced rate preferably ranging from between 30 and 60 beats per minute at rest.

Figure 6:
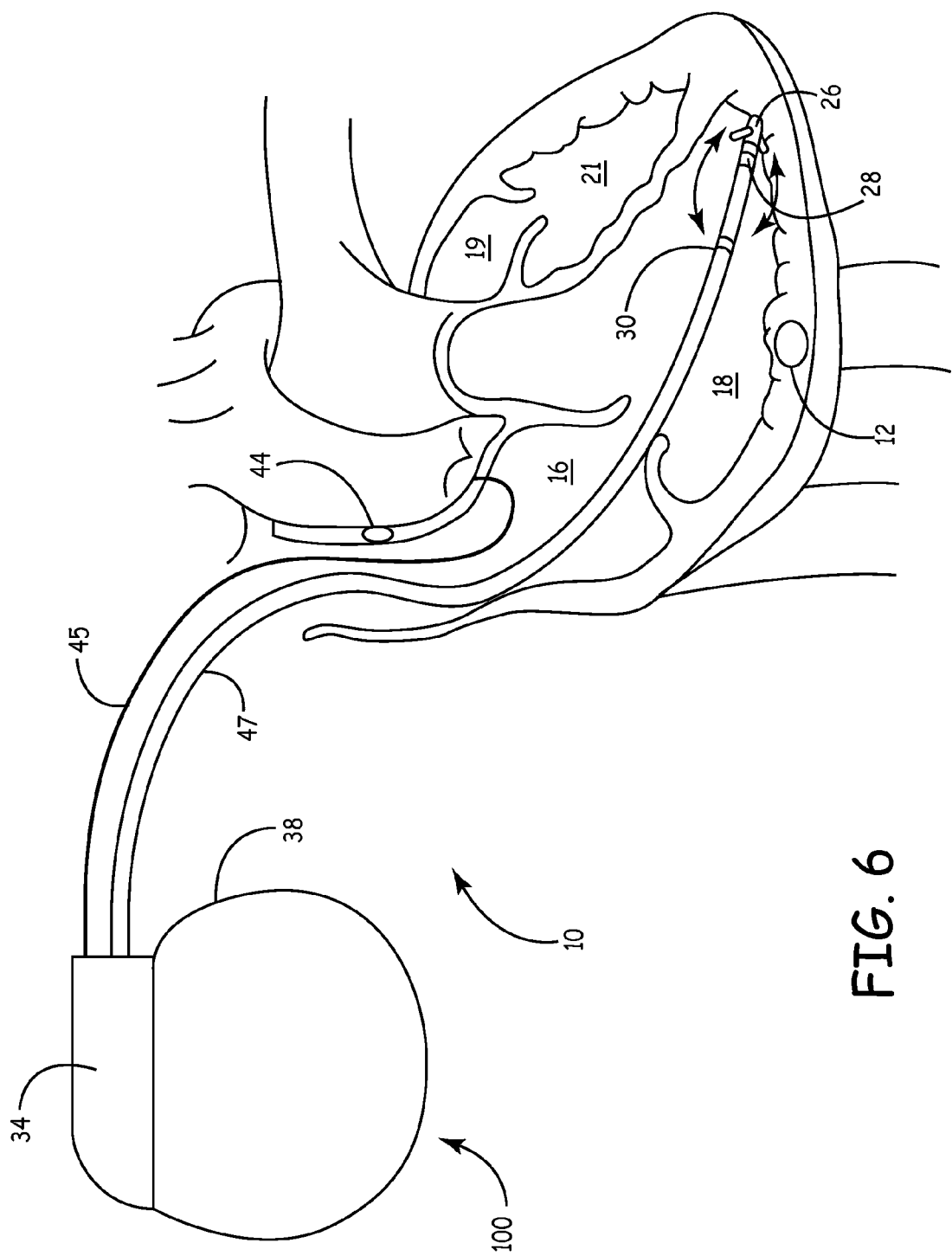
FIG. 6 is a side view of an electronic implantable pacemaker in its functional relation to a heart, which is depicted in cross-section to reveal a plurality of biological pacemakers implanted in the right ventricle and the right atrium according to an embodiment of the invention.

In some situations, a patient's activity level may require faster cardiac pacing than the ICC can produce. Furthermore, it is desirable to have a backup to the biological pacemaker produced from ICC. Turning now to FIG. 6, a backup pacing system 10 is depicted, including a side view of an electronic implantable pacemaker 100 illustrated in its functional relation to a heart, which is depicted in cross-section to reveal the right atrium 16, the left atrium 19, the right ventricle 18, and the left ventricle 21. The depicted implantable pacemaker 100 includes a housing or can 38, a header 34, a right atrial lead 45, and a right ventricular lead 47. The atrial lead 45 extends from the header 38 to the right atrium 16. An electrode 48 carried at a distal end of the atrial lead 45 contacts a wall of the right atrium 16. The right ventricular lead 47 includes a distal fixation device 26, a distal tip electrode 28, and a ring electrode 30. As with the previously-discussed embodiment, a ventricular biological pacemaker 12 is implanted in a wall of the right ventricle 18 and performs a primary pacing function. The implantable pacemaker 100, and specifically the pacing function performed by the right ventricular lead 47, serves as a backup to the ventricular biological pacemaker 12. Although the biological pacemaker 12 is depicted as being implanted in the wall of the right ventricle, other suitable and perhaps preferable implantation locations include the epicardial wall of the left ventricle and the interventricular septum. Furthermore, an atrial biological pacemaker 44 is implanted in a wall of the right atrium 16 and performs a primary pacing function. The implantable pacemaker 100, and specifically the pacing function performed by the atrial lead 45, serves as a backup to the atrial biological pacemaker 44. Although two biological pacemakers 12 and 44 are depicted, it will be appreciated that fewer or more than two biological pacemakers may be employed, and implanted in different heart locations, according to the heart condition and the desired therapy. Furthermore, although in the depicted embodiment both the atrial lead 45 and the right ventricular lead 47 are utilized, fewer or more than two leads may be necessary according to the heart condition and the desired therapy.

Figure 7:
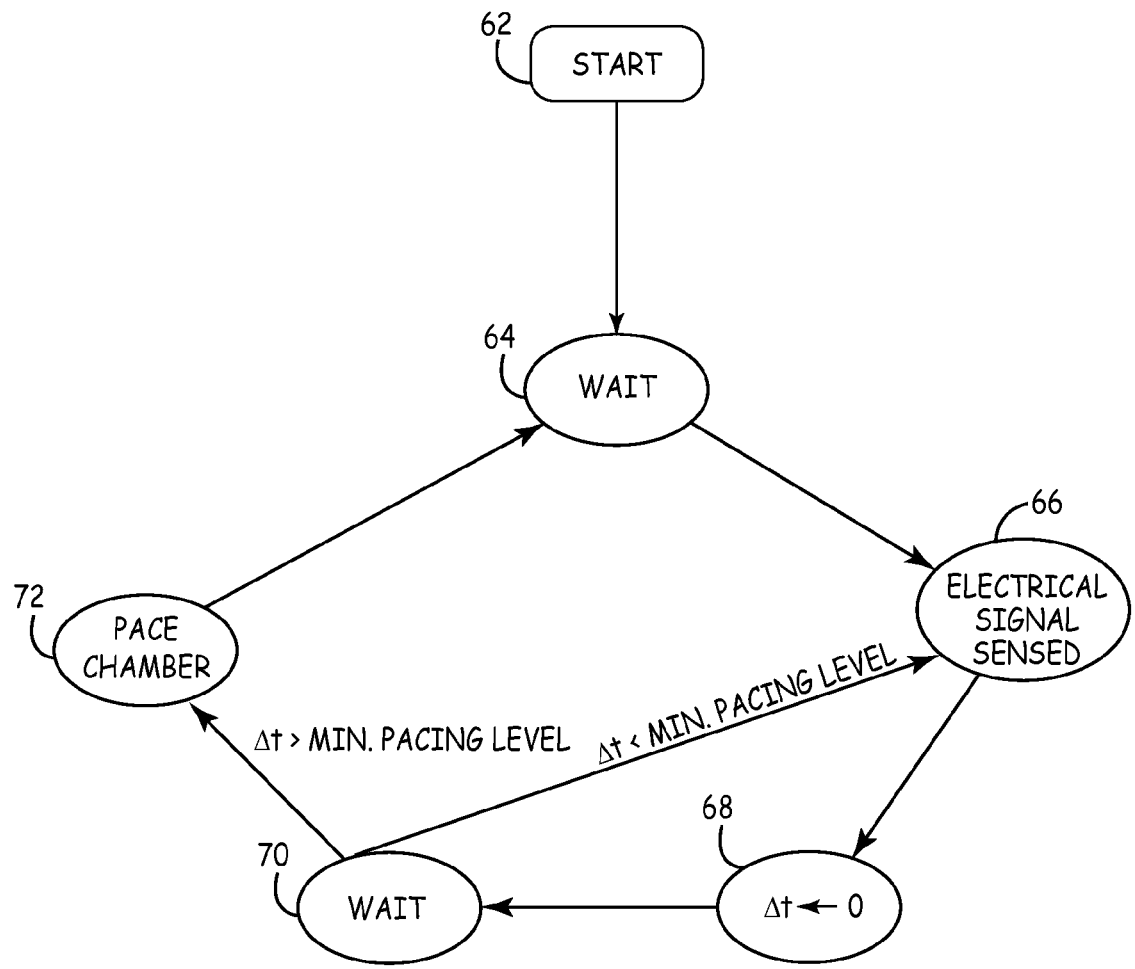
FIG. 7 is a flow chart depicting a method for backing up the pacing functions of a biological pacemaker using an electronic pacemaker according to an embodiment of the invention.

The functions and implementations of the implantable pacemaker 100 and at least one of the biological pacemakers 12 and 44 will next be described in conjunction with the flow chart depicted in FIG. 7. In general, backup pacing using the implantable pacemaker 100 is achieved by transmitting pacing stimuli to the right atrium 16 and the right ventricle 18, although the implantable pacemaker 100 may be implanted into other heart regions to provide pacing stimuli thereto. Within the implantable pacemaker housing 38 is a power source such as a battery, power supply circuitry, sensing and signal processing circuitry, therapy delivery circuitry (which may include pacing as well as cardioversion/defibrillation circuitry), a microprocessor and associated memory, and telemetry circuitry. Atrial stimulation is transmitted to the right atrium 16 through the atrial lead 45 and its associated electrode 48. Pacing stimulation for the right ventricle 18 includes electric pulses that are applied using the tip electrode 28 and the ring electrode 30. The pacing circuitry, including sensing and signal processing circuitry inside the housing 38, generates the pacing pulses delivered through the leads 45 and 47 to the right atrium 16 and the right ventricle 18, respectively. The electrodes 28, 30, and 48 are also used together with the pacing circuitry to derive sensed signals representing the heart's electric activity.

The process starts as step 62, and the implantable pacemaker 100 waits as step 64 until an electrical signal produced by one of the biological pacemakers 12 and 44 is sensed as step 66. For example, if the implantable pacemaker 100 is monitoring electrical activity produced by the ventricular biological pacemaker 12, the electrical signal sensed will typically be an R-wave. Similarly, the sensed electrical signal will be a P-wave if the implantable pacemaker 100 is monitoring electrical activity produced by the atrial biological pacemaker 44. Upon sensing an electrical signal, a timer ΔT is set to zero as step 68. The implantable biological pacemaker 100 then waits for the next electrical signal produced by one of the biological pacemakers 12 and 44 as step 70. If an electrical signal, produced as a result of pacing stimuli from the biological pacemaker, is sensed before the timer exceeds a predetermined minimum pacing interval then the method reverts to step 66, indicating that a signal was sensed. The timer ΔT is then again reset to zero as step 68, and this loop is repeated. However, if no electrical signal, produced as a result of pacing stimuli, is sensed within the predetermined minimum pacing interval then the implantable pacemaker 100 paces the heart region being monitored as step 72. The implantable pacemaker 100 then waits as step 64 for the next electrical signal to be sensed.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for preventing cardiac pacing or conduction dysfunction in a heart, comprising the steps of:
    implanting into cardiac tissue a biological pacemaker comprising a preparation of an effective amount of interstitial cells of Cajal (ICC) to produce or conduct pacing stimuli and thereby modulate cardiac contraction.

2. The method according to claim 1, wherein the step of implanting the biological pacemaker comprises implanting autologous ICC.

3. The method according to claim 1, wherein the step of implanting the biological pacemaker comprises implanting at least one class of cells selected from the group consisting of myoblasts, hematopoietic stem cells, and bone marrow stem cells.

4. The method according to claim 3, wherein the at least one class of cells comprises myoblasts.

5. The method according to claim 1, wherein the step of implanting the biological pacemaker comprises implanting an effective amount of ICC to improve action potential conduction in the heart.

6. The method according to claim 3, wherein the step of implanting the biological pacemaker comprises implanting autologous ICC.

7. The method according to claim 3, wherein the step of implanting the biological pacemaker comprises implanting an effective amount of ICC to improve action potential conduction in the heart.

8. The method according to claim 4, wherein the step of implanting the biological pacemaker comprises implanting autologous ICC.

9. The method according to claim 4, wherein the step of implanting the biological pacemaker comprises implanting an effective amount of ICC to improve action potential conduction in the heart.

* * * * *